US00PP21054P2

(12) United States Plant Patent
Zerr

(10) Patent No.: US PP21,054 P2
(45) Date of Patent: Jun. 8, 2010

(54) POINSETTIA PLANT NAMED 'FISMARS 339'

(50) Latin Name: *Euphorbia pulcherrima*
Varietal Denomination: Fismars 339

(75) Inventor: Katharina Zerr, Höhr-Grenzhausen (DE)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/322,572

(22) Filed: Feb. 4, 2009

(51) Int. Cl.
*A01H 5/00* (2006.01)

(52) U.S. Cl. ..... Plt./307

(58) Field of Classification Search ..... Plt./307
See application file for complete search history.

(56) References Cited

U.S. PATENT DOCUMENTS

PP14,977 P2 * 7/2004 Zerr ..... Plt./307

OTHER PUBLICATIONS

UPOV ROM GTITM Computer Database, GTI Jouve Retrieval Software 2009/04 Citation for 'Fismars 339'.*

Canadian pbr 'Fismars 339' accessed at http://www.inspection.gc.ca/english/plaveg/pbrpov/cropreport/poi/app00007401e.shtml on Mar. 4, 2010.*

* cited by examiner

*Primary Examiner*—Wendy C Haas
(74) *Attorney, Agent, or Firm*—S. Matthew Edwards

(57) ABSTRACT

A new poinsettia plant named 'Fismars 339' particularly distinguished by brilliant red flower color, large, rosette-like, flat inflorescence, dark green, ovate shaped leaves, evenly branching, medium size, good shape for packing and transportation, mid season flowering and good keeping characteristics.

1 Drawing Sheet

Latin name of the genus and species of the plant claimed: *Euphorbia pulcherrima.*

Varietal denomination: 'Fismars 339'.

BACKGROUND OF THE NEW PLANT

The present invention comprises a new Poinsettia plant, botanically known as *Euphorbia pulcherrima,* and hereinafter referred to by the variety name 'Fismars 339.'

'Fismars 339' is a product of a planned breeding program. The new cultivar 'Fismars 339' has brilliant red bracts, dark green foliage, mid season flowering, and about medium sized plant habit.

'Fismars 339' originated from an induced mutation discovered in the parent variety 'Fismars' (U.S. Plant Pat. No. 14,977).

Irradiations of young plants of the variety 'Fismars' had been made in Ahrenburg, Germany, in May 2003. The treated plants were grown out in Hillscheid, Germany, and propagated by shoot cuttings. The resulting plants were screened for positive mutations. In the spring of 2004, a branch mutation was discovered, which was grown and examined as a separate clone.

Horticultural examinations of plants grown from cuttings of the plant were made in the fall to winter of 2005. Examinations continuing thereafter on a larger scale, have demonstrated that the combination of characteristics as herein disclosed for 'Fismars 339' are firmly fixed and are retained through successive generations of asexual reproduction.

'Fismars 339' has not been observed under all possible environmental conditions. The phenotype may vary significantly with variations in environment such as temperature, light intensity and day length.

Plant Breeders' Rights for this cultivar were applied for in the European Union on Jun. 2, 2008 and in Canada on Jul. 4, 2008. 'Fismars 339' has not been made publicly available more than one year prior to the filing of this application.

DESCRIPTION OF DRAWING

The accompanying photographic drawing shows typical flower and foliage characteristics of 'Fismars 339' with colors being as true as possible with an illustration of this type. The photographic drawing is a flowering pot, taken on Dec. 1, 2008, with plants potted in mid July 2008, about 19 weeks old.

DETAILED BOTANICAL DESCRIPTION

The measurements were taken in in Hillscheid, Germany, latitude 50° north, in mid December 2008 on plants that were grown on benches in a greenhouse. Culture of these plants had started in late July 2008 with planting rooted cuttings in 14 cm pots and pinching about 2 weeks later. The plants were grown under natural day light in the fall (no black cloth to initiate earlier flowering) and at the moderately warm temperature of 18° C. for the bench heating.

Color Chart used: Royal Horticultural Society Colour Chart (RHS) 2001

BRIEF SUMMARY OF INVENTION

The following observations, measurements, and comparisons describe plants grown on benches in a greenhouse in Hillscheid, Germany. The following traits have been repeatedly observed and are determined to be basic characteristics of the new variety. The combination of these characteristics distinguishes this Poinsettia plant as a new and distinct variety.

1. Brilliant-red bracts, nearly without any lobes
2. Relatively large, flat, rosette-like inflorescences 3. Dark green foliage, ovate-shaped leaves
4. Medium sized, evenly mounding plant habit
5. Good transportation ability and keeping quality
6. Mid season flowering

DIFFERENCES BETWEEN THE NEW VARIETY 'FISMARS 339' AND A SIMILAR VARIETY

'Fismars 339' differs from 'Fismars' (U.S. Plant Pat. No. 14,977) by having a deeper red bract color, without tendency to fading, and somewhat deeper reddish or brownish coloration of stems and petioles, slightly more compact plant habit. Somewhat later flowering, that is opening of the true flowers, has been observed in several places (locations).

Plant:

*Form, growth and habit.*—Low shrub, evenly branched, with robust stems slanting upright (V-shape), which is good for transportation.
*Plant height* (*without pot*).—33 cm.
*Plant width.*—46 cm.
*Number of branches.*—8.3.
*Number of inflorescences.*—6.6.

Stem:

*Color of stem.*—Ground color green, RHS 146A, middle and upper parts with distinct infusion of anthocyanin, the resulting color is approximately RHS 183C.
*Length of stem.*—Approximately 18–20 cm.
*Internode length.*—3–5 cm.
*Diameter.*—0.6–0.8 cm.
*Texture.*—Glabrous.

Foliage:

*Arrangement.*—Alternate.
*Quantity.*—5–6 leaves per branch.
*Aspect.*—Petioles are more or less horizontally directed, while the leaf blades show slightly downwards.
*Immature leaf color, upper surface.*—RHS 143A.
*Immature leaf color, lower surface.*—RHS 143B.
*Mature leaf color, upper surface.*—Dark green, RHS 139A.
*Lower surface.*—RHS 137A.
*Leaf length.*—12.0–14.5 cm.
*Leaf width.*—8.5–10.5 cm.
*Shape.*—Ovate without or with only a weak degree of lobing.
*Base shape.*—Nearly truncate to weakly rounded.
*Apex shape.*—Acute to acuminate.
*Margin.*—Entire, lobes with rounded or acute tips.
*Texture.*—Flat, smooth, apart from the protruding veins on the under-side, glabrous.
*Color of veins, upper surface.*—Brown, fading from base towards tip, RHS 181A to 181D.
*Color of veins, lower surface.*—RHS 181B to 181D, and pale green, RHS 145C near leaf tip.
*Petiole color, upper surface.*—RHS 185A, deep red-purple.
*Petiole color, lower surface.*—RHS 184A to 185A.
*Petiole length.*—5.5–6.5 cm.
*Diameter of petiole.*—0.3 cm.
*Texture upper and lower surfaces.*—Smooth, glabrous.

Inflorescence:

*Type.*—Terminal cyme with surrounding whorl of colored bracts.
*Flowering, botanically.*—Early to mid December (opening of the stamen, shedding of pollen).
*Start of flowering, commercially* (*sufficiently colored bracts*).—In late November.
*Flowering response time.*—About 9–10 weeks from equinox.
*Duration of flowering.*—Generally good keeping quality, depends on light and environment, at least 4–8 weeks of 'shelf' life.
*Fragrance.*—Absent.
*Shape of inflorescence.*—Rosette-like arrangement, flat, horizontally borne.
*Diameter of inflorescence.*—18–22 cm.
*Inflorescence, vertical diameter.*—3–4.5 cm.
*Number of completely colored bracts per inflorescence* (*sized over 2 cm*).—12–14.
*Single bract, shape.*—Ovate, nearly without any lobes.
*Bract, apex.*—Acuminate.
*Bract, base.*—Rounded or obtuse.
*Single bract, length of blade.*—10.5–11.0 cm, younger bracts diminishing in size.
*Single bract, width of blade.*—6.5–7.3 cm.
*Bract color, upper side.*—RHS 45B, red.
*Bract color, lower side.*—More bluish than RHS 46C.
*Vein color, upper surface.*—Indistinct, similar as bract blade.
*Vein color, lower surface.*—Pink, RHS 51B or 51C, fading towards the leaf tip.
*Texture.*—Flat, smooth, relatively very little rugosity.
*Bract petiole diameter.*—0.3 cm.
*Petiole color, upper surface.*—Deep red, RHS 46A to RHS 53A.
*Petiole color, lower surface.*—Pink, RHS 54A or 54B.

Cyme (true inflorescence):

*Cyme, diameter.*—1.5 cm.
*Number of cyathia.*—Most often 5, borne in a small cluster.
*Cyathium, shape.*—Ovate.
*Cyathium, diameter.*—0.5 cm.
*Cyathium, length.*—0.6 cm.
*Cyathium, color.*—Mainly RHS 144B, top is red, RHS 46C.
*Peduncle length.*—2–3 mm.
*Peduncle color.*—RHS 144C.
*Nectar cups.*—Usually one per cyathium.
*Nectur cup, width.*—Mostly 4 mm.
*Nectar cup, color.*—Golden yellow, RHS 13A to occasionally RHS 17B.

Reproductive organs:

*Stamen* (*actually reduced male florets*).—Usually in a bunch of 15–20 at the top of the cyathium.
*Shape.*—Strap-like.
*Filament length.*—3–4 mm.
*Filament color.*—Red, RHS 46B.
*Anther color.*—Yellow, RHS 11A.
*Anther diameter.*—1 mm.
*Pollen quantity.*—Moderate (normal quantity).
*Pollen color.*—Yellow, RHS 12A.
*Fertility/seed set.*—No seed set observed, but appears fertile.

Disease/pest resistance: Disease resistance or susceptibility has not been observed on this hybrid.

What is claimed is:

1. A new and distinct variety of poinsettia plant named 'Fismars 339,' substantially as illustrated and described herein.

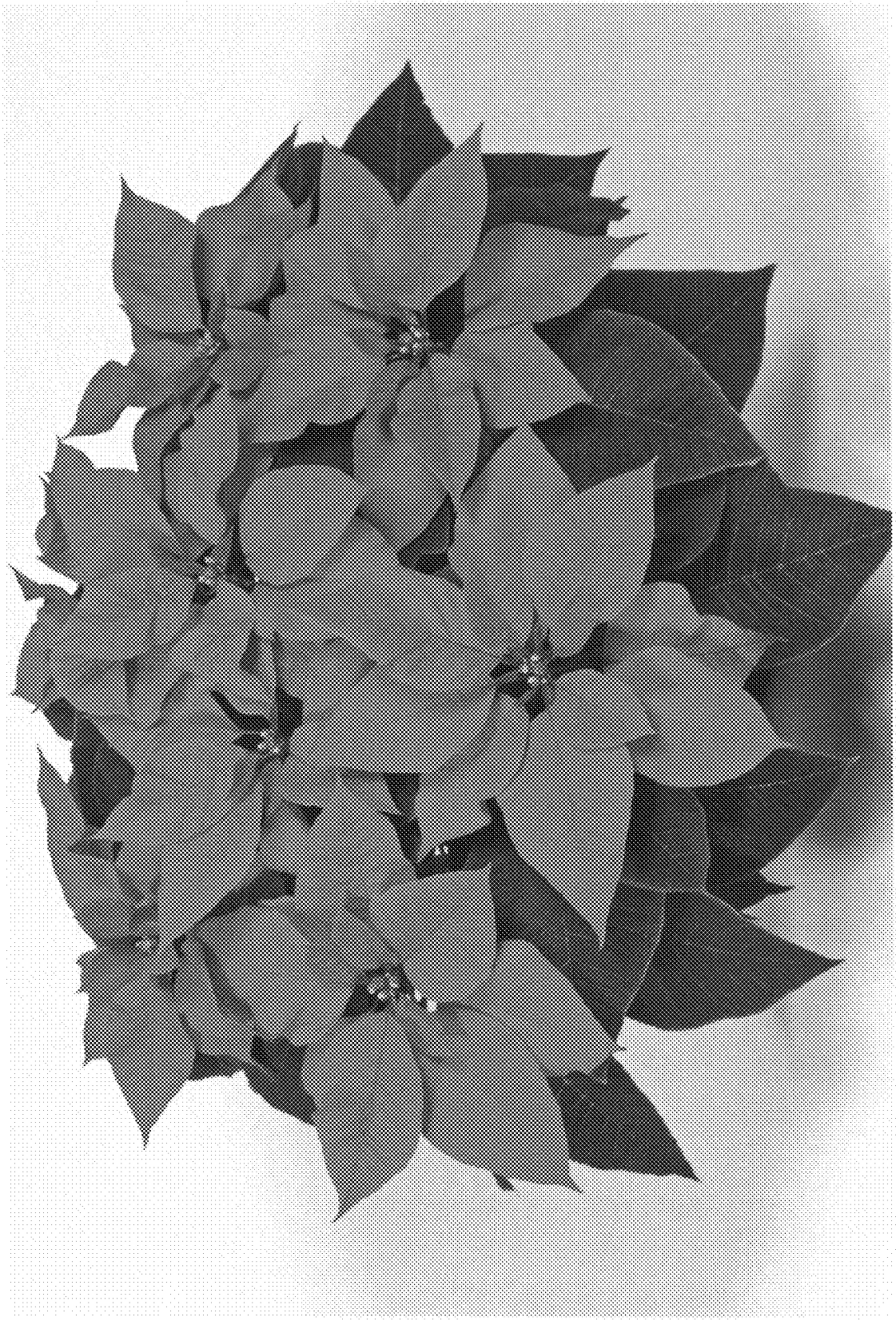

* * * * *